United States Patent [19]
Altemare, Jr.

[11] Patent Number: 6,019,468
[45] Date of Patent: Feb. 1, 2000

[54] SPECTACLE KIT

[76] Inventor: Kenneth D. Altemare, Jr., 438 Deer Park Dr., Jefferson Boro, Pa. 15025

[21] Appl. No.: 09/165,762
[22] Filed: Oct. 2, 1998
[51] Int. Cl.⁷ ..................................................... G02C 1/00
[52] U.S. Cl. ................................. 351/158; 351/156; 2/444
[58] Field of Search ..................... 351/158, 156, 351/57, 41; 2/442, 443, 444, 445, 446, 13

[56] References Cited

U.S. PATENT DOCUMENTS

| | | | |
|---|---|---|---|
| 3,787,113 | 1/1974 | Shedrow | 351/158 |
| 4,023,214 | 5/1977 | Waldherr | 2/444 |
| 4,057,057 | 11/1977 | Backlund | 128/142.4 |
| 4,542,965 | 9/1985 | Shedrow | 351/57 |
| 4,711,539 | 12/1987 | Krusas et al. | 351/63 |
| 4,810,080 | 3/1989 | Grendol et al. | 351/41 |
| 4,951,322 | 8/1990 | Lin | 2/439 |
| 5,170,502 | 12/1992 | Hegendörfer et al. | 2/13 |
| 5,410,763 | 5/1995 | Bollé | 2/436 |
| 5,541,676 | 7/1996 | Pallat | 351/156 |
| 5,657,106 | 8/1997 | Herald, Jr. et al. | 351/158 |

*Primary Examiner*—Huy Mai
*Attorney, Agent, or Firm*—Douglas G. Glantz

[57] ABSTRACT

An article and method are disclosed providing a spectacle kit having a protective mask insert clip and detachable means for attaching a spectacle front piece firmly to the protective mask insert, by snapping the receiver onto an insert clip. Notch attachment means connect a holding strap at each horizontal end of the spectacle front piece. In one embodiment, a first elastic strip and quick-snap fastener, e.g., a Velcro fastener, are connected to a second elastic strip and quick-snap fastener, e.g., a Velcro fastener, to form a ring around the wearer's head such that the spectacle kit can be worn external from the protective mask.

20 Claims, 7 Drawing Sheets

SPECTACLE KIT

BACKGROUND OF THE INVENTION

1. Technical Field

This invention relates generally to spectacle kits. In one aspect, this invention relates to spectacle kits for use with protective masks.

2. Background

Firemen, safety and rescue personnel, and industrial professionals often require the use of protective masks or Self Contained Breathing Apparatus (SCBA). The protective masks are needed to enter hazardous environments, e.g., such as a chemical filled area with caustic gases, or a burning structure. Protective masks also are needed to enter potentially hazardous environments as a safety precaution.

Some sports require the use of protective masks to enter hostile environments. For example, a protective mask is needed in underwater diving.

A person requiring the use of corrective optical lenses for improving visual acuity must be able to use corrective optical lenses while using the protective mask. The use of contact lenses while using the protective mask is impractical because most contact lenses today are soft contact lenses which are manufactured using a material incorporating water in an amount of 38% by weight or more of the water. The soft contact lenses become contaminated by smoke and/or chemicals, thereby making the lenses uncomfortable to wear and/or structurally damaged.

A spectacle kit includes optical lens eye-wear structures supported on the nose or face, commonly called glasses. A spectacle kit today typically uses thermal plastic lenses, e.g., CR39 monomer polycarbonate lenses, to provide the corrective optical lenses.

A spectacle kit is needed for those who must wear protective masks and who also require corrective optical lenses.

One method used in the past, including as used by the military, includes a pair of lens frames connected by a hinged nosepiece to allow the system to be held in a folded mask.

A second method used in the past has had the support structure attach to a back block rigidly mounted inside a face mask. The lenses are removable from the system by pulling the whole unit out of the mask. A slidably releaseable dove-tail connection positions the frame front properly in an up and down adjustment.

INTRODUCTION TO THE INVENTION

Commercially available spectacle kits currently available today for use with a protective mask have several disadvantages. Currently available spectacle kits have too many parts which must be manipulated, and in the course of an emergency, when many protective masks are needed to be worn, a user does not have time to manipulate the many parts.

Another disadvantage is found with current lens sizes which are small and reduce peripheral vision.

A type of spectacle kit includes the suction cup method. A suction cup is placed directly on the face plate. Many times, the suction cup does not retain suction, but rather dislodges from the face plate after a short time period, thereby rendering the user helpless.

Another type of spectacle kit is cemented directly onto the face plate and is permanently sealed to the face plate, thereby preventing the user from removing the spectacle kit.

Another disadvantage is found when a back block is rigidly mounted inside the face mask. In many cases, face masks are not always worn by the same person. A volunteer fire department, for example, may only have a limited number of face masks, and those masks may need to be worn by different persons. Moreover, some of the multiple users may not require the use of corrective lenses.

The rigidly mounted back block may not be in the proper position for a different user. Or, the rigidly mounted back block may be in the proper position in the mask, but the user may not require a spectacle kit, thereby necessitating the expenditure of critical time and the execution of awkward maneuvers for removing the fixed spectacle kit from the mask. On the other hand, if no spectacle kit is mounted in the mask, the user requiring a spectacle kit in the mask must take the critical time and make the awkward maneuvers needed for placing the fixed spectacle kit into the mask.

Another disadvantage lies in the fact that when a user must remove the mask, the spectacle kit must remain in the mask thereby removing his vision correction. In this case, the user is forced to locate his or her own eyeglasses or use nothing at all. The user trying to locate his or her own eyeglasses must do so without vision correction, because the spectacle kit remains behind in the mask. If the user options to use his or her own eyeglasses, the user must find a protective location for the eyeglasses while they are stored such that they will not become scratched or broken and rendered unusable.

In emergencies, many situations arise which require a protective mask to be worn without notice. When such an emergency situation does arise, a person has to manipulate and think about many items. A safety spectacle kit which allows a person to think about fewer items, which reduces the number of items which the person is required to manipulate, and which allows that person to keep his or her mind on other safety matters, would be of significant importance. Such a safety spectacle kit would be beneficial to provide a quick and easy method of providing a vision correction system in a protective mask.

A detachable spectacle kit is needed for use with protective masks.

A universal spectacle kit is needed for use with protective masks. A universal spectacle kit may be used outside the protective mask by those requiring corrective optical lens eye wear and also may be used inside a full face protective mask. The universal spectacle kit and full face protective mask must retain a seal for respiration. Currently available eye wear has temple earpieces or a thin strap which breaks the tight seal around the user's face, which tight seal is mandatory for the user's protection.

It is an object of the present invention to provide a spectacle kit article and method for use with protective masks to be used by persons requiring prescription lenses.

It is an object of the present invention to provide a spectacle kit article and method for use with a protective mask to be used by persons having different needs such as those requiring tinted lenses or other specialty lenses.

It is an object of the present invention to provide a detachable spectacle kit article and method for use with a protective mask.

It is another object of the present invention to provide a simple means and method of inserting and removing a spectacle kit from a protective mask wherein the inserting and removing the spectacle kit may be accomplished without hassle or fear of losing any component pieces.

It is a further object of the present invention to provide a universal spectacle kit article and method for use inside or outside of a protective mask, such that a wearer may use the spectacles when he or she has removed himself or herself from the situation requiring the protective mask.

It is an object of the present invention to provide a spectacle kit article and method for providing prescription or non prescription lenses to be used outside the Self Contained Breathing Apparatus (SCBA) for safety eye-wear protection.

It is still a further object of the present invention to provide a detachable spectacle kit article and method to provide interchangeability with regard to protective masks such that the same spectacle kit may be used in several different protective masks effectively and without having components that require a rigid mount to a protective mask.

These objects and additional objects and features of the present invention can be understood more completely by referencing the following detailed description of the preferred embodiments in conjunction with the drawings.

SUMMARY OF THE INVENTION

The article of the present invention includes a spectacle front piece housing two lenses, a bridge piece, and a receiver, a protective mask insert having an insert clip at a central location, and detachable means for attaching the spectacle front piece firmly to the protective mask insert, by snapping the receiver on the insert clip.

A method of the present invention includes the steps of providing a spectacle front piece having two lenses, providing a bridge piece and a receiver on the spectacle front piece, providing a protective mask insert having an insert clip at a central location of the protective mask insert, and detachably attaching the spectacle front piece to the protective mask insert, wherein the spectacle front piece firmly attaches to the insert clip by snapping the receiver on the insert clip.

In one aspect, the spectacle front piece further includes notch attachment means for connecting a holding strap at each horizontal end of the spectacle front piece. In one embodiment, a first elastic strip and Velcro fastener are connected to a second elastic strip and Velcro fastener to form a ring around the wearer's head such that the spectacle kit can be worn external from the protective mask.

DETAILED DESCRIPTION OF THE PREFERRED EMBODIMENTS

Figure 1:
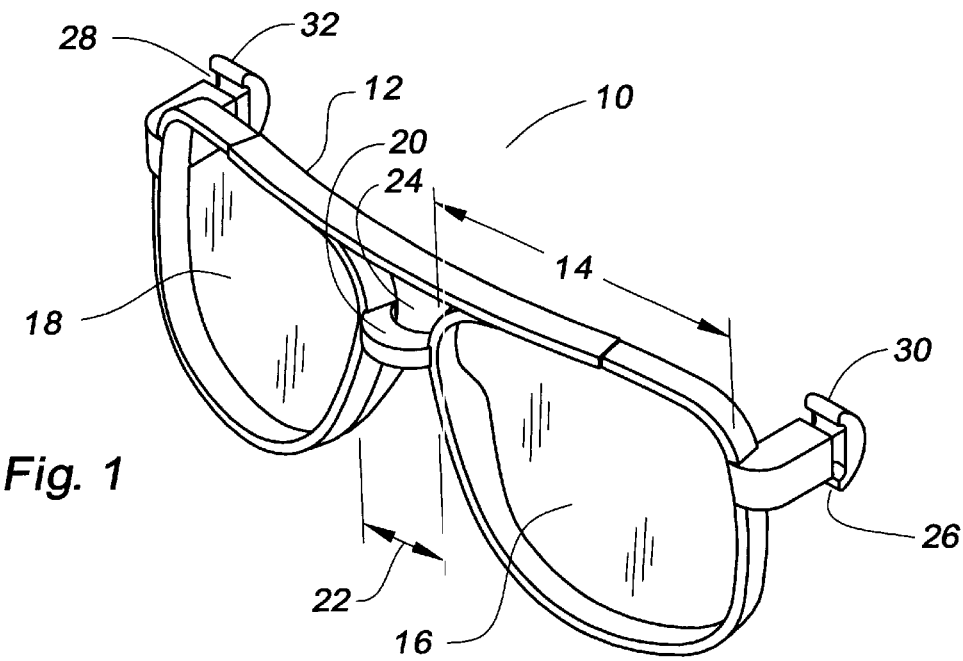
FIG. 1 shows a front perspective view of a front piece of the present invention.

The novel spectacle kit and method of the present invention provide means and method for inserting eye wear into conventional, commercially available full-face respirators and Self Contained Breathing Apparatus (SCBA).

The novel spectacle kit includes a front piece having an appropriately constructed bridge with an appropriately constructed nosepiece attached to the bridge. The front piece houses the lenses and provides a generously wide field of view. Small notch attachments are located at the ends of the front piece and hold elasticized straps which enable the entire front piece to be attached easily and comfortably to the wearer's head for quick convenient use outside of the mask.

The novel spectacle kit further includes an insert, which is the snap-on stabilizing point for the front piece. The insert itself is able to snap in and out of the mask with extreme ease and speed.

The novel spectacle kit has many advantages over currently existing spectacle kits, including worry-free access to fires and chemical situations for those firemen, paramedics, or servicemen requiring eyeglasses, without the concern for where to place their glasses while in the respiration equipment. In addition, the front piece and snap-on, front-piece-receiver insert allows for the quick transition from (1) wearing the respirator or SCBA into a paramedic or rescue mode, and then to (2) when outside of a "hot-zone," a simple pop of the front piece or front piece and insert out of the mask.

The novel spectacle kit provides a more convenient way to make the transition from wearing the face masks with eye wear to wearing the eye wear alone, or vice versa. The attachment also is cost effective as the insert can be removed and installed in all similar masks in a fire or safety department.

The front piece requires and provides a large field of view to increase the peripheral field of view, without compromising an eyeglass prescription. Prior art front pieces are limited to 48 mm. The front piece of the present invention has a significantly broader visibility, e.g., of 50 mm and larger. The front piece has a saddle bridge for comfort on the nose of those who wear it. In addition, the front piece provides unique end pieces which allow for unique attachment of the elastic straps which enable attachment of the front piece to the face outside of the mask.

The pliable plastic insert, e.g., of nylon, is easily inserted into the mask and receives the front piece as a snap-on fit in one formed piece to provide a snug attachment within the mask. The front piece snaps onto and off of the insert. The front piece can be removed from the mask and placed onto the face of the user with the elastic straps for use outside of the mask. This creates two options for the user, either leaving the insert in the mask and removing only the front piece to place onto the user for use outside of the mask, or to remove the entire piece. Both options have been found to work efficiently.

The present invention provides a novel spectacle kit for use in protective masks, e.g., such as by way of example, in a Self Contained Breathing Apparatus (SCBA). The term spectacle kit is meant to include a frame front and optical lenses for improving the visual acuity of a wearer.

In one aspect, the present invention provides a novel spectacle kit for use in a protective mask which requires only two pieces for application and use in the protective mask.

To overcome problems with conventional spectacle kits, the present invention has only two pieces with a very simple connection between the first and second pieces. A first piece in the form of a protective mask insert slips into a protective mask, and the second piece in the form of a spectacle front piece snaps together with the first piece.

In one aspect, the present invention provides a novel spectacle kit which also can be used as protective eye wear without the protective mask.

A pair of optical lenses are contained in the spectacle front piece which snaps onto and off of a protective mask insert.

The protective mask insert is placed into a protective mask or SCBA Self Contained Breathing Apparatus and is held firmly by a tight, tension-mounted press fit. The protective mask insert can remain in the protective mask without impairing vision and can be used by anther person with his or her spectacle kit front piece. Or, the spectacle kit front piece can be removed from the protective mask by simply unsnapping it from the protective mask insert.

The front piece then can be worn as a conventional pair of spectacles by using elastic straps with quick-snap fasteners which are attached to two temple end pieces, e.g., such as a pair of quick-snap fasteners provided by Velcro fasteners attached to two temple end pieces. The elastic strap creates an adjustable band that fits snugly around a wearer's head. The elastic strap remains on the temple end pieces at all times, when inside the mask each side is tucked down in each side of the mask.

The spectacle kit insert may be left inside one or all of the protective masks in a fire department or safety department without impairing the user's vision. This universal aspect is attractive for a fire department or a safety department wherein many different individuals may use the same mask, e.g., in the case of volunteer fire departments. The spectacle kit front piece having lenses of the user's prescription can be kept and secured in the user's possession until its next use.

Referring now to FIG. 1, a front piece 10 is shown. The front piece 10 includes a spectacle front 12, preferably constructed of a durable nylon material, preferably of a smoke gray or crystal color. The front piece 10 provides a large viewing width 14, for each lens 16 and 18, e.g., such as by way of example, in a dimension of 46 mm up to 52 mm. The front piece 10 is constructed such that a bridge 20 has a width 22 of 16 mm up to 20 mm, preferably about 18 mm to 19 mm, to provide maximum comfort to the wearer.

A receiver 24 is constructed directly above the bridge 20.

An end notch attachment 26 and an opposite end notch attachment 28 are constructed at a first end 30 and a second end 32, respectively, of the front piece 10. The notch attachments 26 and 28 are constructed such that peripheral vision impairment is minimized, and nearly non-existent.

Figure 2:
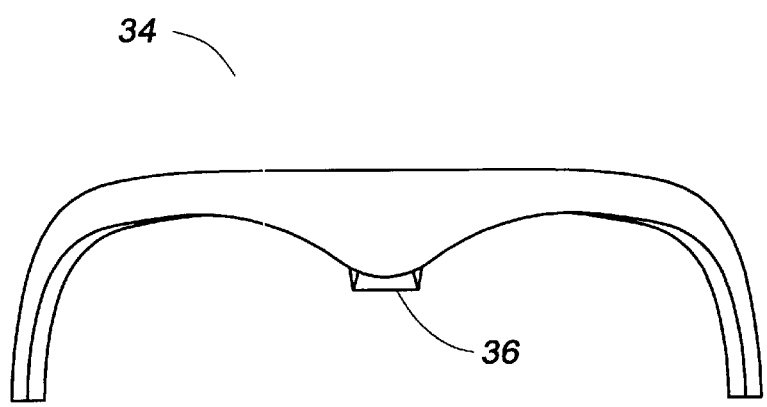
FIG. 2 shows a front elevation view of a protective mask insert of the present invention.

Referring now to FIG. 2, a protective mask insert 34 is shown. The protective mask insert 34 contains an insert clip 36 which is centrally located on the protective mask insert 34. The insert clip 36 is specifically adapted to snap into the receiver 24 of the front piece 10. The insert clip 36 allows easy transition of the front piece 10 to stand alone or to be connected with the protective mask insert 34.

The protective mask insert 34 is constructed in two sizes, small and large, respectively. A small protective mask insert has dimensions of about 6 inches wide, about 2 inches high on each side, with a thickness of about 0.100 inches, proportionate to fit inside a small protective mask or a small SCBA mask such as the MSA mask available from the Mine Safety Appliance Company of Pittsburgh, Pa. or such as the Draeger mask available from the Draeger Company of Pittsburgh, Pa. A large protective mask insert has dimensions of about 7 inches wide, about 1 inch high on each side, with a thickness of about 0.100 inches, proportionate to fit inside large protective masks and SCBA masks such as the MSA Elite mask available from the Mine Safety Appliance Company of Pittsburgh, Pa., and such as the Scott mask available from the Scott Company of Monroe, N.C.

The protective mask insert 34 is constructed preferably of nylon material of a preferably smoke gray or crystal color. Other colors which may be used in place of crystal and smoke gray include, but are not limited to tan, black, flesh-tone and crystal gray.

Figure 3:
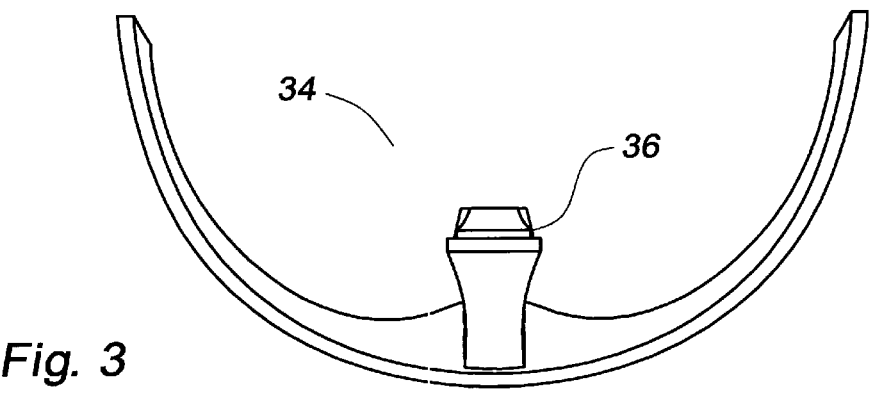
FIG. 3 shows a top plan view of a protective mask insert of the present invention.

Referring now to FIG. 3, a top plan view of the protective mask insert 34 is shown, along with a view of the insert clip 36. The insert clip 36 of the protective mask insert 34 attaches to the receiver 24 of the front piece 10 simply and quickly by snapping the front piece 10 to the insert clip 36 at the receiver 24.

Figure 4:
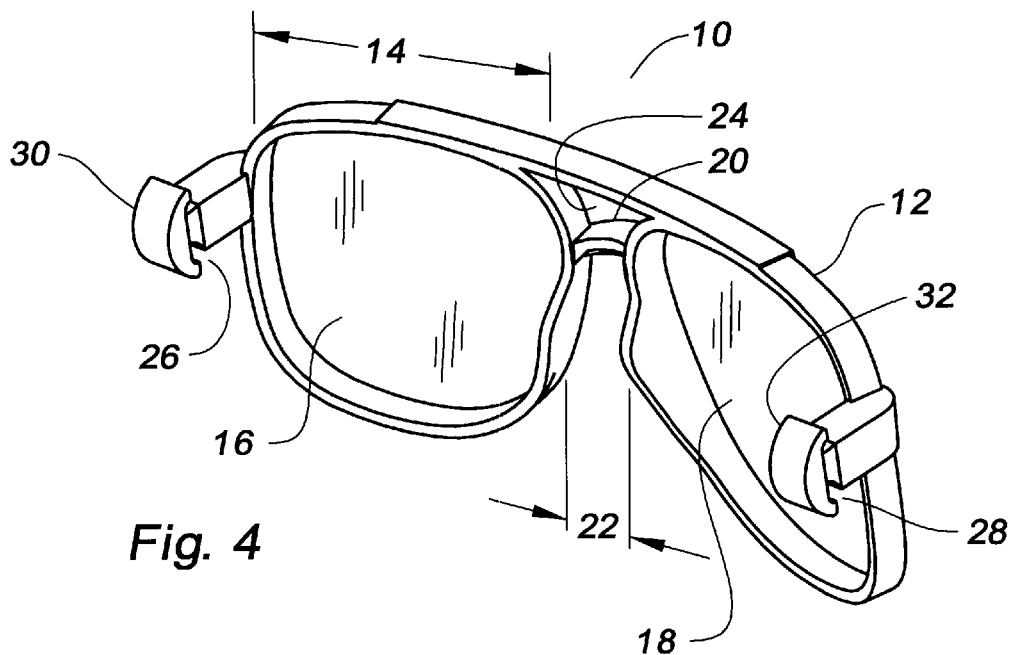
FIG. 4 shows a rear perspective view of a front piece of the present invention.

Referring now to FIG. 4, a rear perspective view of the front piece 10 is shown. The receiver 24 provides a location to attach the front piece 10 to the protective mask insert 34 at the insert clip 36. Further, the notch attachments 26 and 28 provide a means for the spectacle kit to be used outside of a protective mask.

Figure 5:
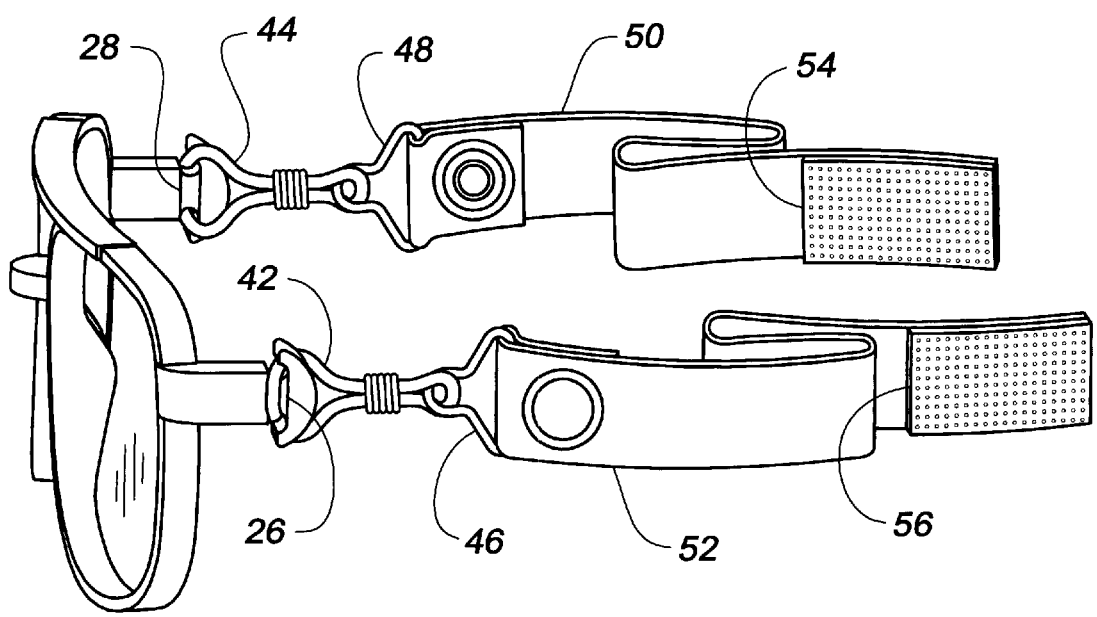
FIG. 5 shows a side perspective of a pair of notch attachments of the present invention and attached elastic bands.

Referring now to FIG. 5, a perspective rear view of the notch attachments 26 and 28 are shown with elastic straps 50 and 52 attached. A notch attachment buckle 42 and a corresponding opposite notch attachment buckle 44 slide over notch attachments 26 and 28, respectively, to form the connection of the elastic straps 50 and 52 to the front piece 10. The notch attachment buckle 42 affixes to a buckle clip 46. Likewise, the notch attachment buckle 44 affixes to a buckle clip 48. The buckle clips 46 and 48 attach to the elastic straps 50 and 52. The elastic strap 50 has a strip 54 made of a detachable quick-snap fastener material, e.g., such as Velcro, sewn onto it. The elastic strap 52 has a corresponding Velcro strip 56 sewn onto it. The Velcro strips 54 and 56 can be connected to form a ring, such that the front piece 10 can be used outside of a protective mask.

The elastic straps 50 and 52 can be left in place while the spectacle kit is in use in a protective mask as they will not interfere or impede the utility or purpose of the protective mask. Each side 50 and 52 is tucked down in its respective side, out of the line of sight of the user. The spectacle kit of the present invention can be worn outside the protective mask. This external use of the spectacle kit of the present invention can benefit the users of protective masks in that they will not have to worry about carrying a second pair of eyeglasses for use outside of a safety or protective mask.

Figure 6:
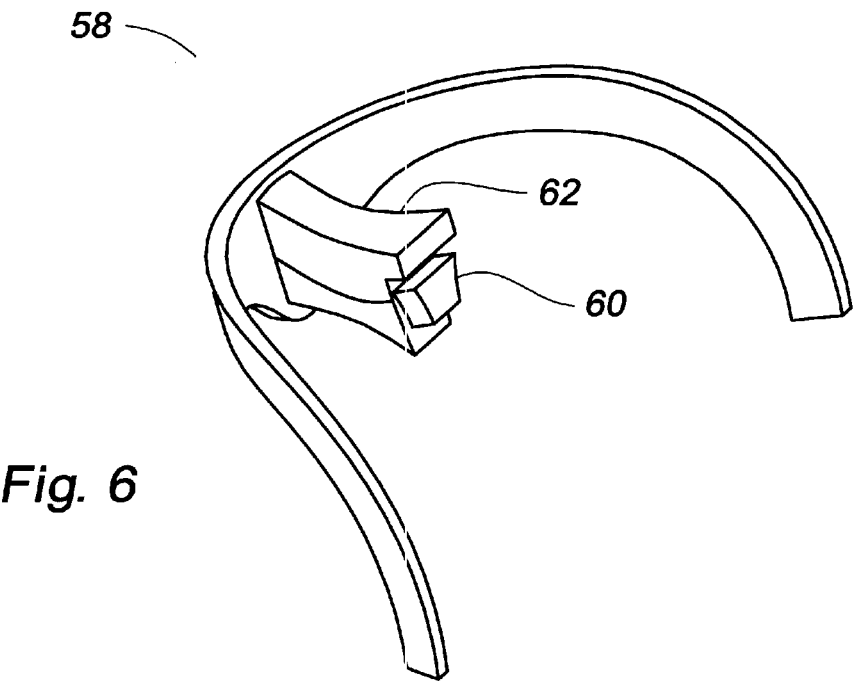
FIG. 6 shows a rear perspective view of a small protective mask insert of the present invention.

Referring now to FIG. 6, a small protective mask insert 58 is shown. An insert clip 60 is specific to the protective mask insert 58 in that the length of protrusion 62 of the insert clip 60 from the protective mask insert 58 is configured specifically for smaller protective and SCBA masks to insure a proper positioning of the frame front for the best possible optics to provide improved user vision and comfort.

Figure 7:
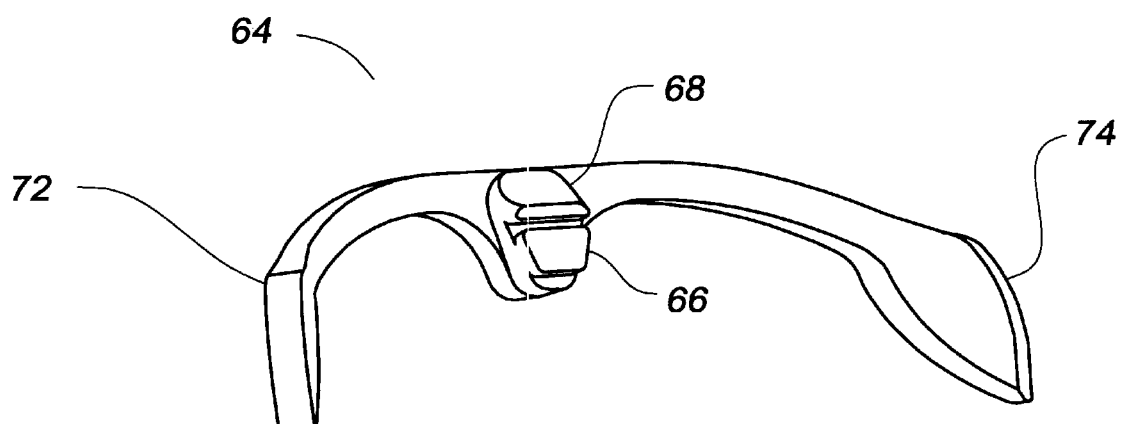
FIG. 7 shows a rear perspective view of a large protective mask insert of the present invention.

Referring now to FIG. 7, a large protective mask insert 64 is shown. An insert clip 66 is specific to the protective mask insert 64 in that the length of protrusion 68 of the insert clip 66 from the protective mask insert 64 is designed specifically for larger protective and SCBA masks to insure a proper positioning of the frame front for the best possible optics to provide improved user vision and comfort.

The large protective mask insert 64 has enlarged ends 72 and 74 to provide more support for the insert in the larger protective masks. The large protective mask insert 64 has a radius larger than the small insert 58 to provide a flatter curvature and a more tight press fit with less movement in the larger protective masks.

The length of protrusion 62 of the protective mask insert 58 is greater than the corresponding length of protrusion 68 of the protective mask insert 64.

Figure 8:
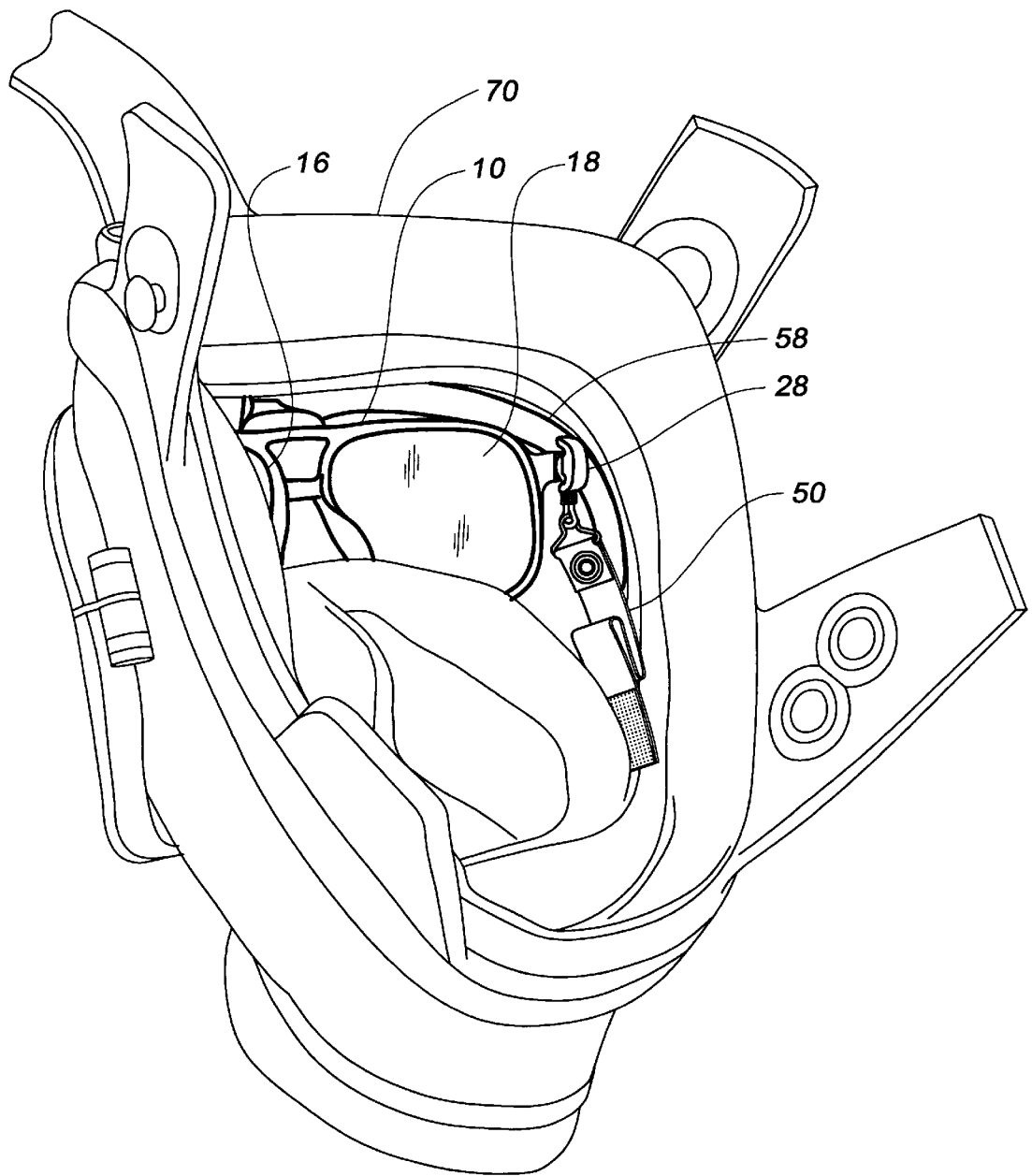
FIG. 8 shows a rear perspective view of an MSA mask with a small protective mask insert of the present invention in place.

Referring now to FIG. 8, an MSA mask 70 is shown with protective mask insert 58. The protective mask insert 58 is attached to mask 70 simply by inserting the protective mask insert 58 into the proper position inside the mask such that the connection between the inert 58 and the front piece 10 can be made and properly allow the wearer to see through the lenses 16 and 18. The protective mask insert 58 will be held into place by the pressure the protective mask insert 58 exerts on the top and sidewalls of the mask 70. The notch attachment 28 is positioned in such a way that it does not break the tight seal of the mask. The elastic strap 50 is attached to notch attachment 28 and is folded to be concealed so as not to impair the user's vision.

Figure 9:
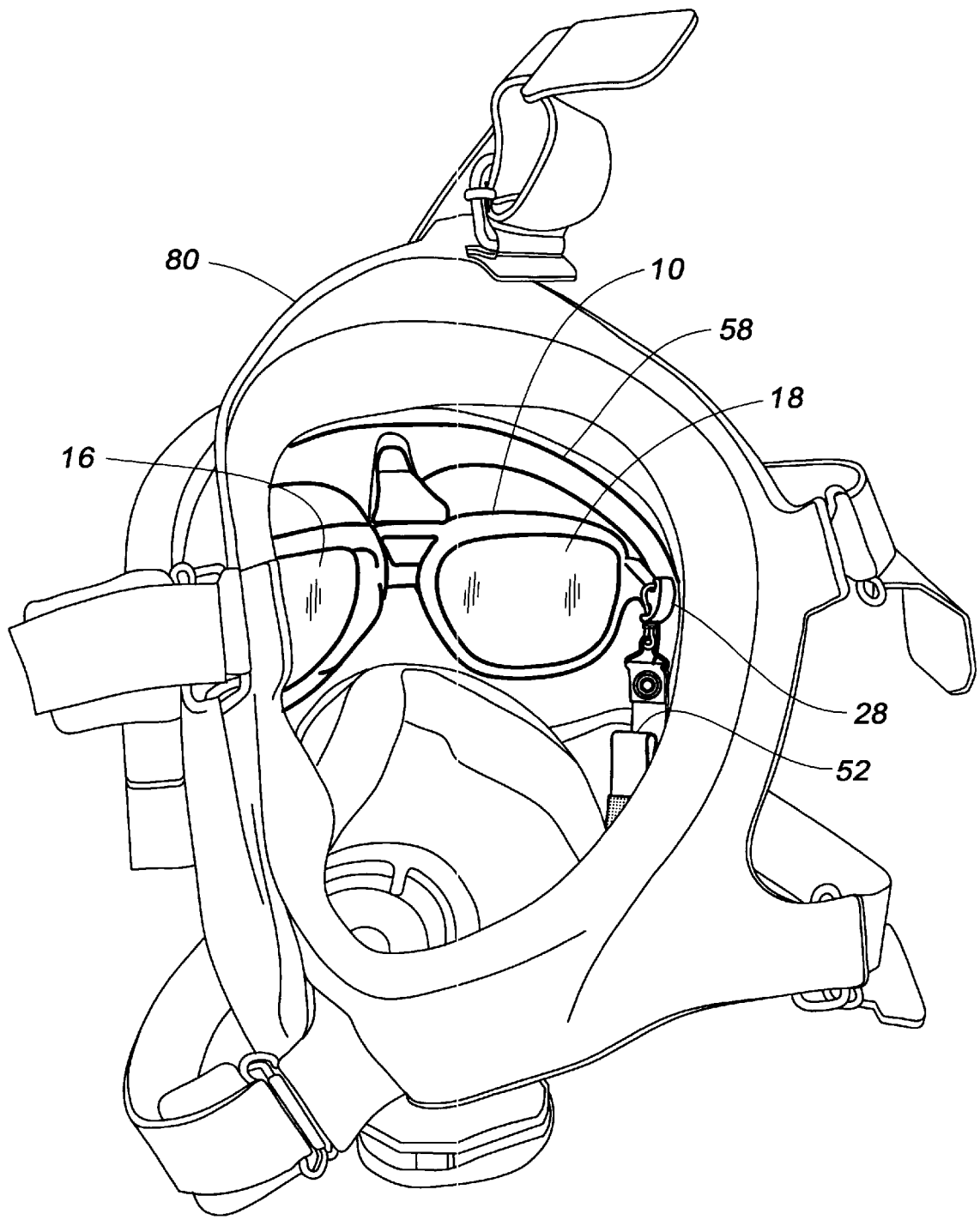
FIG. 9 shows a rear perspective view of Draeger mask with a small protective mask insert of the present invention in place.

Referring now to FIG. 9, a Draeger mask 80 is shown with protective mask insert 58. The protective mask insert 58 is attached to mask 80 simply by inserting the protective mask insert 58 into the proper position inside the mask such that the connection between the insert 58 and the front piece 10 can be made and properly allow the wearer to see through the lenses 16 and 18. The protective mask insert 58 will be held into place by the pressure the protective mask insert 58 exerts on the top and sidewalls of the mask 80. The notch attachment 28 is positioned in such a way that it does not break the tight seal of the mask. The elastic strap 50 is attached to notch attachment 28 and is folded to be concealed so as not to impair the user's vision.

Figure 10:
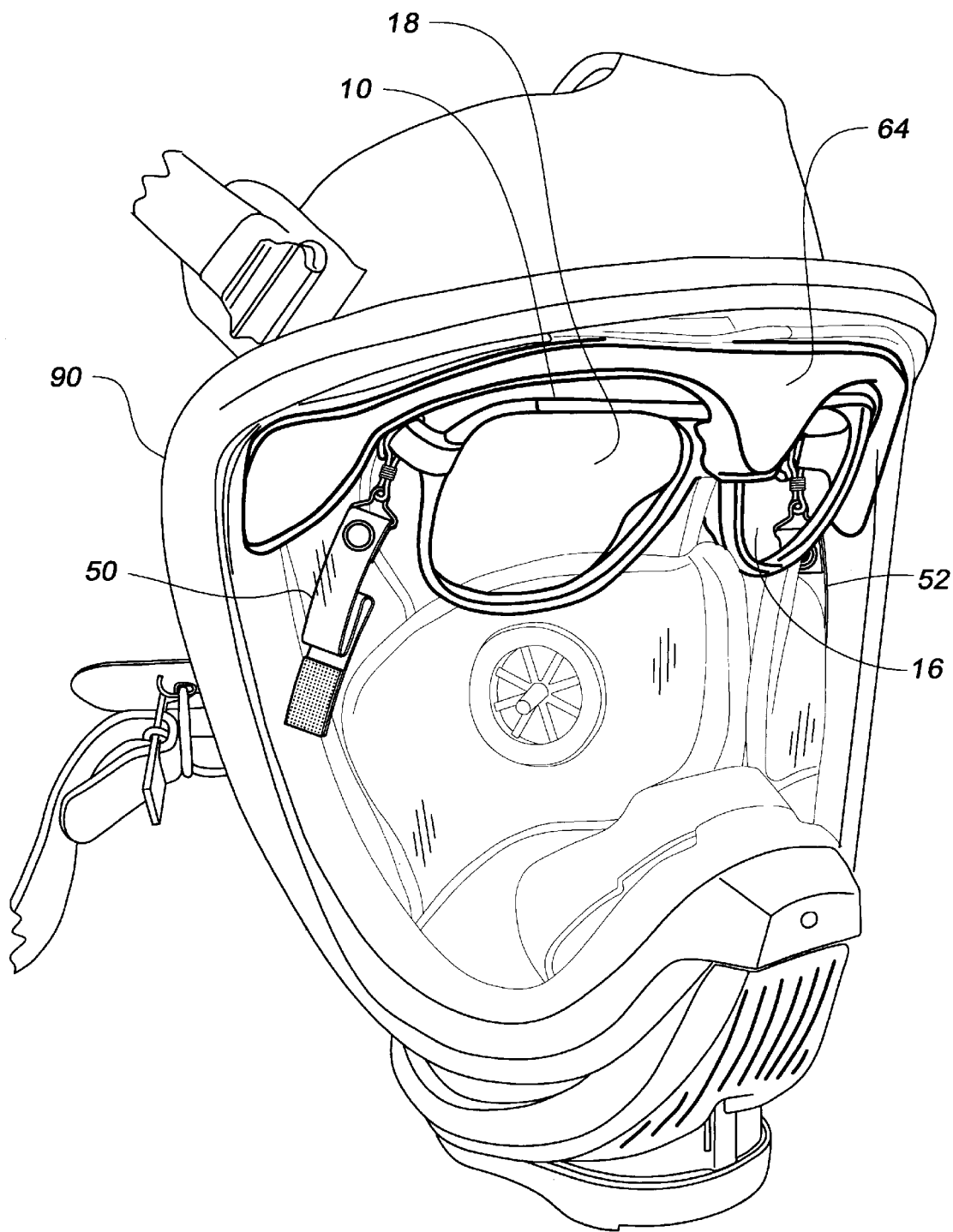
FIG. 10 shows a front perspective view of an MSA Elite mask with a large protective mask insert in place.

Referring now to FIG. 10, an MSA Elite mask 90 is shown with protective mask insert 64. The protective mask insert 64 is attached to mask 90 simply by inserting the protective mask insert 64 into the proper position inside the mask such that the connection between the insert 64 and the front piece 10 can be made and properly allow the wearer to see through the lenses 16 and 18. The protective mask insert 64 will be held into place by the pressure the protective mask insert 64 exerts on the top and sidewalls of the mask 90. The elastic strap 50 is folded and concealed so as not to impair the user's vision.

Figure 11:
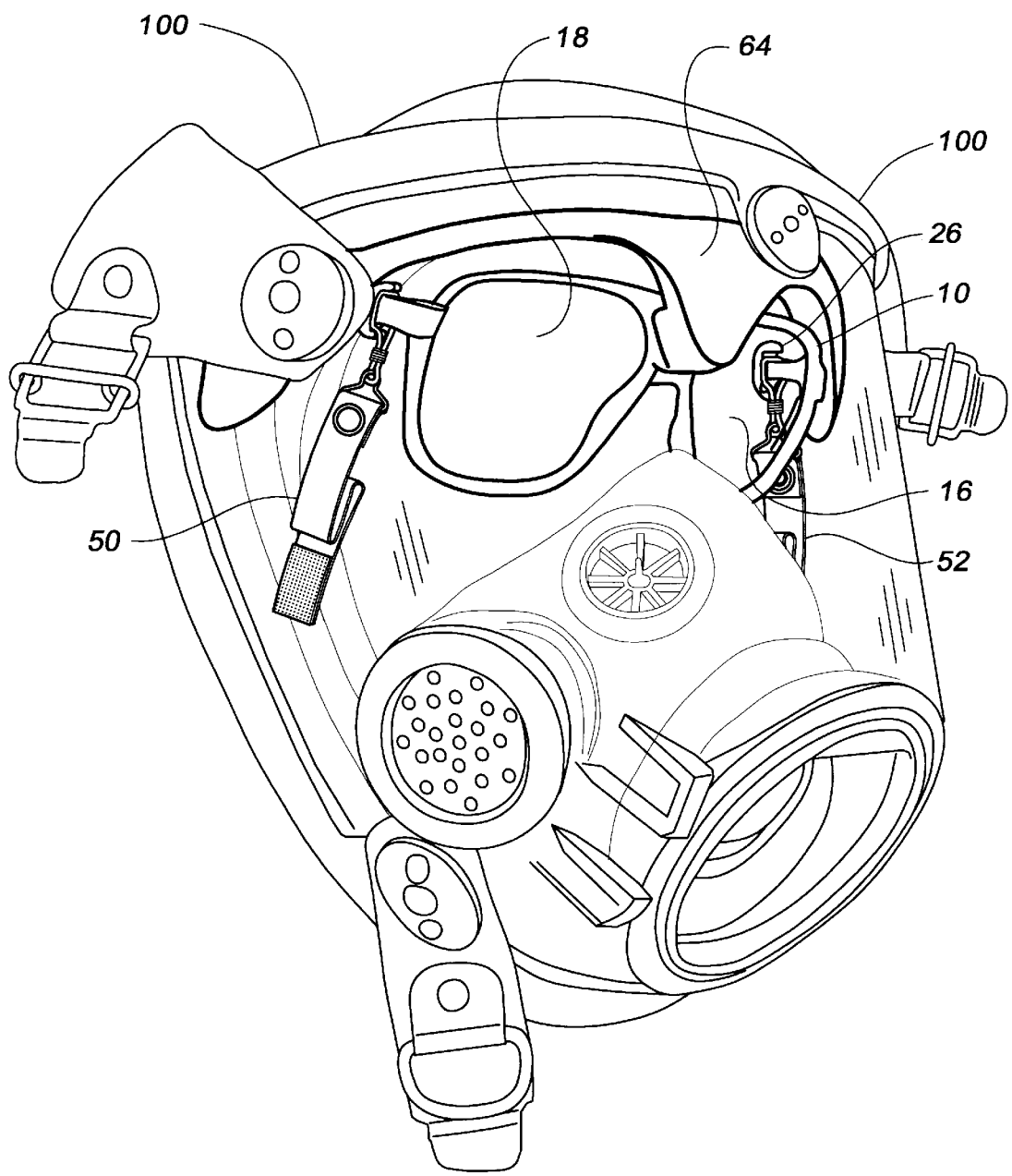
FIG. 11 shows a front perspective view of a Scott mask with a large protective mask insert in place.

Referring now to FIG. 11, a Scott mask 100 is shown with protective mask insert 64. The protective mask insert 64 is attached to mask 100 simply by inserting the protective mask insert 64 into the proper position inside the mask such that the connection between the insert 64 and the front piece 10 can be made and properly allow the wearer to see through the lenses 16 and 18. The protective mask insert 64 will be held into place by the pressure the protective mask insert 64 exerts on the sidewalls of the mask 100. The notch attachment 26 is positioned in such a way that it does not break the tight seal of the mask. The elastic straps 50 and 52 are attached to notch attachment 26 and 28, respectively, and are folded to be concealed so as not to impair the user's vision.

The spectacle kit and method of the present invention provide two parts including a frame front and an insert piece. Both pieces are easily insertable and removable from a protective mask. The frame front is larger for enhanced peripheral vision and houses two corrective optical lenses having the user's prescription for proper vision inside the mask. The frame front housing the corrective optical lenses can be removed from the mask and worn as a safety pair of spectacles by using the attached strap to form a secure fit around the user's head. Currently commercially available spectacle kits can be used only when the mask is being worn by the user, but the spectacle kits of the present invention have corrective lenses in a frame front which can be used inside of or outside of the protective mask. The spectacle kits of the present invention can be provided for all types of protective masks and SCBA's.

The article and method of the present invention include means and method for providing a quickly detachable spectacle kit attachment for gas masks, full respirators, and self contained breathing apparatus used professionally by fire fighters, chemical workers, miners, or the like.

The one-piece front piece of the present invention houses the lenses and provides a generously wide field of view. The present invention includes an appropriately constructed bridge on the one-piece front piece with an appropriately constructed nose piece attached to the bridge.

The one-piece mask insert piece of the present invention is the stabilizing point for the front and is made of a pliable material, e.g., such as nylon, to make it able to snap in and out of the mask with extreme ease and speed.

The one-piece front piece of the present invention provides small notch attachments located at the ends of the front piece for holding elasticized straps which enable the entire front piece to be attached easily and comfortably to the wearer's head for quick, convenient use outside of the mask.

The present invention has advantages over commercially available spectacle kits, including worry-free access to fires and chemical emergencies for those firemen, paramedics, or servicemen requiring the assistance of eye glasses to enable them to do their jobs appropriately, without the concern for where to place their glasses while in the respiration equipment. In addition, the present invention allows for a quick transition from wearing the respirator or SCBA in a "hot-zone," to a paramedic or rescue mode when outside of the hot-zone, with the quick transition out of the mask and quick placement on the wearer's face. The present invention also is cost effective for those requiring its unique service.

The present invention provides a large enough field of view to include the peripherals, without compromising an eyeglass prescription. Prior art fronts are limited to prescription lenses of 44–48 mm. The present invention provides for a preferred prescription lens of 50 mm or more.

The front piece of the present invention has a saddle bridge for comfort on the nose of those who wear it.

In addition, the front piece of the present invention provides enhanced usability, having unique end pieces which will allow for attachment of Velcro straps which enable attachment of the eye kit to the face outside of the mask.

The importance of the differences of the present invention for full-face respirators and Self Contained Breathing Apparatus (SCBA) relates to the ability of the present invention to provide a more convenient way to make the transition into wearing the face-mask and from wearing the face-mask with eye wear to wearing the eye wear alone.

The ability to make the transition from one face mask to another, e.g., "in the time of battle" as when fighting a fire is critically important. Fixedly mounted inserts can not be removed when a gas mask goes bad or when a face shield melts or is degraded in some way. The present invention spectacle kit, on the other hand, can be quickly and completely switched from one face mask to another.

While the invention has been described in conjunction with several embodiments, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

What is claimed is:

1. A spectacle kit article, comprising:
    a) a spectacle front piece having a housing for two lenses, a bridge piece, a receiver, and notch attachment means for connecting a holding strap at each horizontal end of said spectacle front piece;
    b) a removable protective mask insert for placement in a conventional, commercially available full face respirator or self contained breathing mask, said protective mask insert having an insert clip at a central location of said protective mask insert; and
    c) detachable means for attaching said spectacle front piece to said removable protective mask insert, wherein said spectacle front piece firmly attaches to said insert clip by snapping said receiver onto a central protrusion on said insert clip.

2. A spectacle kit article as set forth in claim 1, wherein said insert clip central protrusion has a length configured specifically for positioning of said spectacle front piece on a specific conventional, commercially available full face respirator or self contained breathing mask.

3. A spectacle kit article as set forth in claim 1, wherein said spectacle front piece comprises a one-piece spectacle front piece.

4. A spectacle kit article as set forth in claim 3, wherein said spectacle front piece further comprises a first notch attachment on a first horizontal end and a second notch attachment on a second horizontal end of said spectacle front piece.

5. A spectacle kit article as set forth in claim 4, further comprising an elastic band for forming a ring around a wearer's head such that said spectacle front piece can be worn external from said protective mask and further comprising a buckle clip and a notch attachment buckle on said elastic band.

6. A spectacle kit article as set forth in claim 5, wherein said elastic band further comprises a first elastic strip having a Velcro fastener and a second elastic strip having a Velcro fastener, wherein said first elastic strip connected to said second elastic strip forms a ring around a wearer's head such that said spectacle kit can be worn external from said protective mask.

7. A spectacle kit article as set forth in claim 3, wherein said lenses are larger than 45 mm.

8. A spectacle kit article as set forth in claim 3, wherein said bridge piece is larger than 17 mm.

9. A spectacle kit article as set forth in claim 1, wherein said removable protective mask insert comprises a one-piece removable protective mask insert.

10. A spectacle kit article as set forth in claim 1, wherein said receiver is constructed directly above said bridge, thereby to attach to said removable insert clip at a central location of said protective mask insert by receiving said protrusion for insertion into said receiver on said insert clip.

11. A protection method, comprising:
    a) providing a spectacle front piece having a housing for two lenses, a bridge piece, a receiver, and notch attachment means for connecting a holding strap at each horizontal end of said spectacle front piece;
    b) providing a removable protective mask insert for placement in a conventional, commercially available full face respirator or self contained breathing mask having an insert clip at a central location of said protective mask insert; and
    c) providing detachable means for attaching said spectacle front piece to said removable protective mask insert, wherein said spectacle front piece firmly attaches to said insert clip by snapping said receiver onto a central protrusion on said insert clip.

12. A protection method as set forth in claim 11, further comprising configuring said insert clip central protrusion for a specific conventional, commercially available full face respirator or self contained breathing mask.

13. A protection method as set forth in claim 11, wherein said providing a spectacle front piece comprises providing a one-piece spectacle front piece.

14. A protection method as set forth in claim 13, wherein said providing a spectacle front piece further comprises providing a first notch attachment on a first horizontal end and a second notch attachment on a second horizontal end of said spectacle front piece.

15. A protection method as set forth in claim 14, further comprising an elastic band for forming a ring around a wearer's head such that said spectacle front piece can be worn external from said protective mask and further comprising a buckle clip and a notch attachment buckle on said elastic band.

16. A protection method as set forth in claim 13, wherein said lenses are larger than 45 mm.

17. A protection method as set forth in claim 13, wherein said bridge piece is larger than 17 mm.

18. A protection method as set forth in claim 11, wherein said providing a removable protective mask insert comprises providing a one-piece protective mask insert.

19. A protection method as set forth in claim 11, wherein said receiver is constructed directly above said bridge, thereby to attach to said removable insert clip at a central location of said protective mask insert by receiving said protrusion for insertion into said receiver on said insert clip.

20. A spectacle kit article for use with a protective safety mask, comprising:
    a) a one-piece spectacle front piece having a housing for two lenses larger than 45 mm, a bridge piece larger than 17 mm, and a receiver;
    b) a removable one-piece protective mask insert for placement in a conventional, commercially available full face respirator or self contained breathing mask, said protective mask insert having an insert clip protrusion for insertion into said receiver on said insert clip at a central location of said protective mask insert;
    c) detachable means for attaching said spectacle front piece to said protective mask insert, wherein said spectacle front piece firmly attaches to said insert clip by snapping said receiver on said insert clip;
    d) notch attachment means on said spectacle front piece for connecting a holding strap at each horizontal end of said spectacle front piece comprising a first notch attachment on a first horizontal end and a second notch attachment on a second horizontal end of said spectacle front piece;
    e) an elastic band comprising a first elastic strip having a Velcro fastener and a second elastic strip having a Velcro fastener, wherein said first elastic strip connected to said second elastic strip forms a ring around a wearer's head such that said spectacle kit can be worn external from said protective mask.

* * * * *